US009506916B2

(12) United States Patent
Ripoll et al.

(10) Patent No.: US 9,506,916 B2
(45) Date of Patent: Nov. 29, 2016

(54) METHOD FOR A HIGHLY SENSITIVE DETECTION AND QUANTIFICATION OF BIOMOLECULES USING SECONDARY ION MASS SPECTROMETRY (SIMS) AND RELATED TECHNOLOGIES

(71) Applicant: Biosims Technologies, Rouen (FR)

(72) Inventors: Camille Ripoll, Bihorel (FR); Victor Norris, Bois Guillaume (FR); Gradimir Misevic, Riehen (CH); Guillaume Legent, Martainville-Épreville (FR); Anthony Delaune, Saint Saire (FR)

(73) Assignee: BioSIMS Technologies, Rouen (FR)

( * ) Notice: Subject to any disclaimer, the term of this patent is extended or adjusted under 35 U.S.C. 154(b) by 637 days.

(21) Appl. No.: 13/928,812

(22) Filed: Jun. 27, 2013

(65) Prior Publication Data

US 2013/0338029 A1 Dec. 19, 2013

Related U.S. Application Data

(62) Division of application No. 12/921,606, filed as application No. PCT/IB2009/052735 on Mar. 12, 2009, now abandoned.

(60) Provisional application No. 61/035,803, filed on Mar. 12, 2008, provisional application No. 61/143,504, filed on Jan. 9, 2009.

(51) Int. Cl.
| | |
|---|---|
| G01N 23/225 | (2006.01) |
| G01N 33/68 | (2006.01) |
| G01N 33/543 | (2006.01) |

(52) U.S. Cl.
CPC ........ *G01N 33/543* (2013.01); *G01N 23/2258* (2013.01); *G01N 33/6848* (2013.01); *G01N 2458/15* (2013.01)

(58) Field of Classification Search
CPC .......... G01N 33/543; G01N 33/6848; G01N 23/2258; G01N 2458/15
See application file for complete search history.

(56) References Cited

U.S. PATENT DOCUMENTS

2004/0137491 A1* 7/2004 Okamoto ............. G01N 23/225
435/6.11

OTHER PUBLICATIONS

Kawasaki (Ann. N.Y. Acad. Sci., 2004, 1020:92-100).*
Belu, A.M., et al., "Enhanced TOF-SIMS imaging of a micropatterned protein by stable isotope protein labeling," Anal. Chem., vol. 73(2) (Jan. 15, 2001) pp. 143-150.
Brandt, O., et al., "Development towards label- and amplification-free genotyping of genomic DNA," Appl. Surface Sci., vol. 252(19) (Jul. 30, 2006) pp. 6935-6940.
Brandt, O., et al., "PNA microarrays for hybridization of unlabelled DNA sample," Nucleic Acids Research, col. 31(19) (2003) pp. 1-9.

(Continued)

*Primary Examiner* — Jeremy C Flinders
(74) *Attorney, Agent, or Firm* — Blank Rome LLP

(57) ABSTRACT

The present invention relates to a method for detecting and quantifying the presence or absence of a number of biomolecules in a sample using the SIMS technique and arrays for use in said method.

7 Claims, 4 Drawing Sheets

(56) References Cited

OTHER PUBLICATIONS

Brodie, E., et al., "Abstract 99: Profiling Microbial Identity and Activity: Novel Applications of NanoSIMS and High Density Microarrays," Genomics: GTL Awardee Workshop VI and Metabolic Engineering Working Group Interagency Conference on Metabolic Engineering (Feb. 10, 2008) pp. 93-94.

Dauphas, S., et al., "Localization and Quantitative Analysis of Antigen-Antibody Binding on 2D Substrate Using Imaging NanoSIMS," Anal. Chem., vol. 80 (2008) pp. 5958-5962.

Galli Marxer, C., et al., "Supported membrane composition analysis by secondary ion mass spectrometry with high lateral resolution," vol. 88(4) (Apr. 2005) pp. 2965-2975.

Kraft, M., et al., "Phase Separation of Lipid Membranes Analyzed with High-Resolution Secondary ion Mass Spectrometry," Science, vol. 313 (Sep. 29, 2006), pp. 1948-1951.

Kraft, et al., Supporting Online Material for "Phase Separation of Lipid Membranes Analyzed with High-Resolution Secondary ion Mass Spectrometry," Science, vol. 313 (Sep. 29, 2006), pp. 1948-1951.

Lechene, C., et al., "High-resolution quantitative imaging of mammalian and bacterial cells using stable isotope mass spectrometry," J. Biol., vol. 5(6) (Oct. 5, 2006) pp. 20.1-20.30.

Lechene, C.P., et al., "Quantitative Imaging of Nitrogen Fixation by Individual Bacteria within Animal Cells," Science, vol. 317 (5844) (Sep. 2007) pp. 1563-1566.

Pett-Ridge, J. et al., "Microarrays + NanoSIMS: Linking Microbial Identity and Function with 'NanoSIP'," Second Annual DOE Joint Genome Institute User Meeting (Mar. 28, 2007) pp. 1-4, 48-49.

International Preliminary Report on Patentability dated Sep. 14, 2010 for Application No. PCT/IB2009/052735.

International Search Report dated Oct. 21, 2009 for Application No. PCT/IB2009/052735.

Kraft et al., *Phase Separation of Lipid Membranes Analyzed with High-Resolution Secondary Ion Mass Spectrometry*, www.sciencemap.org/cgi/content/full/313/5795/1948/DC1, Sep. 29, 2006, Science 313, 1948 (2006).

* cited by examiner

SEQUENCE LISTING

<160> NUMBER OF SEQ ID NOS: 4

<210> SEQ ID NO 1
<211> LENGTH: 298
<212> TYPE: DNA
<213> ORGANISM: artificial sequence
<220> FEATURE:
<223> OTHER INFORMATION: probe PML

<400> SEQUENCE: 1

```
tgtctccaat acaacgacag cccagaagag gaagtgcagc cagacccagt gccccaggaa      60
ggtcatcaag atggagtctg aggaggggaa ggaggcaagg ttggctcgga gctccccgga     120
gcagcccagg cccagcacct ccaaggcagt ctcaccaccc cacctggatg gaccgcctag     180
ccccaggagc cccgtcatag gaagtgaggt cttcctgccc aacagcaacc acgtggccag     240
tggcgccggg gaggcagagg aacgcgttgt ggtgatcagc agctcggaag actcagat      298
```

<210> SEQ ID NO 2
<211> LENGTH: 21
<212> TYPE: DNA
<213> ORGANISM: artificial sequence
<220> FEATURE:
<223> OTHER INFORMATION: primer forward PML

<400> SEQUENCE: 2

```
tgtctccaat acaacgacag c                                                21
```

<210> SEQ ID NO 3
<211> LENGTH: 21
<212> TYPE: DNA
<213> ORGANISM: artificial sequence
<220> FEATURE:
<223> OTHER INFORMATION: primer reverse PML

<400> SEQUENCE: 3

```
atctgagtct tccgagctgc t                                                21
```

<210> SEQ ID NO 4
<211> LENGTH: 309
<212> TYPE: PRT
<213> ORGANISM: artificial sequence -continued

```
<220> FEATURE:
<223> OTHER INFORMATION: amino acids 32-327 protein A Staphylococcus
      aureus

<400> SEQUENCE: 4

Met Gly Ser Ser His His His His His Ser Ser Gly Pro Ala Ala
1               5                   10                  15

Asn Ala Ala Gln His Asp Glu Ala Gln Gln Asn Ala Phe Tyr Gln Val
                20                  25                  30

Leu Asn Met Pro Asn Leu Asn Ala Asp Gln Arg Asn Gly Phe Ile Gln
            35                  40                  45

Ser Leu Lys Asp Asp Pro Ser Gln Ser Ala Asn Val Leu Gly Glu Ala
50                      55                      60

Gln Lys Leu Asn Asp Ser Gln Ala Pro Lys Ala Asp Ala Gln Gln Asn
65                  70                      75                  80

Asn Phe Asn Lys Asp Gln Gln Ser Ala Phe Tyr Glu Ile Leu Asn Met
                85                      90                  95

Pro Asn Leu Asn Glu Ala Gln Arg Asn Gly Phe Ile Gln Ser Leu Lys
                100                 105                 110

Asp Asp Pro Ser Gln Ser Thr Asn Val Leu Gly Glu Ala Lys Lys Leu
            115                 120                 125

Asn Glu Ser Gln Ala Pro Lys Ala Asp Asn Asn Phe Asn Lys Glu Gln
130                 135                 140

Gln Asn Ala Phe Tyr Glu Ile Leu Asn Met Pro Asn Leu Asn Glu Glu
145                 150                 155                 160

Gln Arg Asn Gly Phe Ile Gln Ser Leu Lys Asp Asp Pro Ser Gln Ser
                165                 170                 175

Ala Asn Leu Leu Ser Glu Ala Lys Lys Leu Asn Glu Ser Gln Ala Pro
                180                 185                 190

Lys Ala Asp Asn Lys Phe Asn Lys Glu Gln Gln Asn Ala Phe Tyr Glu
                195                 200                 205

Ile Leu His Leu Pro Asn Leu Asn Glu Glu Gln Arg Asn Gly Phe Ile
                210                 215                 220

Gln Ser Leu Lys Asp Asp Pro Ser Gln Ser Ala Asn Leu Leu Ala Glu
225                 230                 235                 240

Ala Lys Lys Leu Asn Asp Ala Gln Ala Pro Lys Ala Asp Asn Lys Phe
                245                 250                 255

Asn Lys Glu Gln Gln Asn Ala Phe Tyr Glu Ile Leu His Leu Pro Asn
                260                 265                 270

Leu Thr Glu Glu Gln Arg Asn Gly Phe Ile Gln Ser Leu Lys Asp Asp
            275                 280                 285

Pro Ser Val Ser Lys Glu Ile Leu Ala Glu Ala Lys Lys Leu Asn Asp
            290                 295                 300

Ala Gln Ala Pro Lys
305
```

METHOD FOR A HIGHLY SENSITIVE DETECTION AND QUANTIFICATION OF BIOMOLECULES USING SECONDARY ION MASS SPECTROMETRY (SIMS) AND RELATED TECHNOLOGIES

This application is a divisional of U.S. patent application Ser. No. 12/921,606, filed Sep. 9, 2010, titled Method For A Highly Sensitive Detection And Quantification Of Biomolecules Using Secondary Ion Mass Spectrometry (SIMS) And Related Technologies. This application is related to and claims priority to PCT/IB2009/052735 filed Mar. 12, 2009, U.S. Provisional Patent Application No. 61/143,504 filed Jan. 9, 2009 and U.S. Provisional Patent Application No. 61/035,803, filed Mar. 12, 2008, each of which are hereby incorporated by reference in their entirety.

FIELD OF THE INVENTION

The invention relates to a method for detection and quantification of biomolecules, such as DNA, RNA or proteins, using isotope labeling and secondary ion mass spectrometry, and arrays designed for carrying out said method.

BACKGROUND OF THE INVENTION

In the early sixties, Castaing and Slodzian developed mass-filtered emission ion microscopy using secondary ions, which is part of a technique later named secondary ion mass spectrometry (SIMS). With this technique, a beam of ions (the primary ion beam) is used as a probe to sputter the surface atomic layers of a sample into atoms or atomic clusters, a small fraction of which are ionized. In a SIMS instrument, these secondary ions are separated according to mass and are then used to measure a secondary ion current to create, for example, a quantitative atomic mass image of the analyzed surface.

SIMS has become a major tool in semiconductor and surface science studies, geochemistry, the characterization of organic material, and cosmochemistry. However, ion microscopy has been for a long time considered only as a marginal method for solving problems in life sciences, due mainly to poor lateral resolution (1-0.5 μm) and insufficient mass separation power.

Technological and conceptual improvements led to significant progress in both lateral resolving power and mass resolution, in particular due to the use of a finely focused primary ion beam. SIMS microscopy has therefore become a very powerful imaging tool. For example, Lechene et al. were able using the SIMS technique to image individual stereocilia, the mechanosensory organelles of the inner cells of the cochlea (Lechene at al. Journal of Biology, 2006, 5:20). In another experiment, they were able to study the nitrogen fixation in bacteria cultured in a $^{15}N$ atmosphere. The use of SIMS technique also allowed Lechene et al. to localize, quantify and compare nitrogen fixation in single cells and subcellular structures (Lechene et al. Science 2007, 317:1563). Thus, SIMS technology is now widely used for imaging cells or tissues, and is a powerful tool for diagnostic.

SIMS technique was also used to detect hybridization of unlabelled DNA to microarrays of peptide nucleic acids (PNA) (Brandt et al, 2003, Nucleic Acids Research, 31:19). In these experiments, PNA/DNA or PNA/RNA duplexes were visualized by SIMS detecting the phosphates that are an integral part of the nucleic acids but are completely missing in PNA.

The invention aims to provide a method for detecting and quantifying the presence or absence of a number of biomolecules in a sample using the SIMS technique. The method described in Brandt et al. presents the following drawbacks: (i) it can only be applied with PNA probes or probes that do not contain phosphates and (ii) it does not allow quantification of the interaction probe/target. Therefore, the Applicant aims to provide a universal method that can be applied to a great number of samples for the detection and the quantification of a great number of interaction probe/targets in each sample using the SIMS technique, the detection and the quantification of said interactions being determined by the calculation of the isotopic ratio probe/target (see FIG. 1).

SUMMARY OF THE INVENTION

The present invention relates to an array comprising a substantially planar substrate having a conducting surface and a number of discrete areas containing probes being labeled with at least one rare, stable or unstable isotope or exogenous isotope.

According to one embodiment, said substantially planar substrate having a conducting surface is a silicon wafer.

According to one embodiment, said probes are labeled with at least one heavy stable isotope selected in the group $^{2}H$, $^{13}C$, $^{15}N$, $^{17}O$, $^{18}O$, $^{33}S$, $^{34}S$ and $^{36}S$, or with at least one unstable isotope selected in the group $^{3}H$ and $^{14}C$ or with at least one exogenous isotope selected in the group of $^{79}Br$ and $^{81}Br$.

According to one embodiment, said array is a microarray wherein each discrete area has one of the dimensions length, width or diameter being from 1 μm to 1000 μm.

According to one embodiment, each discrete area is a microwell that comprises probes being labeled with at least one rare, stable or unstable isotope or exogenous isotope.

According to one embodiment, said array is a nanoarray wherein each discrete area has one of the dimensions length, width or diameter being from 1 nm to 1000 nm.

According to one embodiment, each discrete area is a nanowell that comprises probes being labeled with at least one rare, stable or unstable isotope or exogenous isotope.

According to one embodiment, each microwell comprises a number of nanowells, and said nanowells comprise the probes being labeled with at least one rare, stable or unstable isotope or exogenous isotope.

The present invention relates to a method for detecting and quantifying in at least one sample the presence or absence of at least one biomolecule, comprising:
 (a) contacting said at least one sample with an array as described here above,
 (b) washing and drying the array,
 (c) detecting and counting by SIMS the common secondary ions along with the corresponding rare secondary ions.

According to one embodiment, each sample to be tested is contacted with one or more discrete area of the array.

According to one embodiment, said sample to be tested is a single cell.

According to one embodiment, said method is for determining a molecular atlas of the sample tested, wherein said molecular atlas is the determination of the transcriptome, proteome, lipidome, metabolome, glycome and/or interactome of said sample.

According to one embodiment, said method is for predicting a predisposition to a disease, or for diagnosing a disease in a subject in need thereof.

According to one embodiment, said method is for monitoring the efficacy of a therapeutic agent administrated to a subject to treat a disease.

According to one embodiment, said method is for screening therapeutic agents.

DETAILED DESCRIPTION OF THE INVENTION

Definitions

Figure 1:
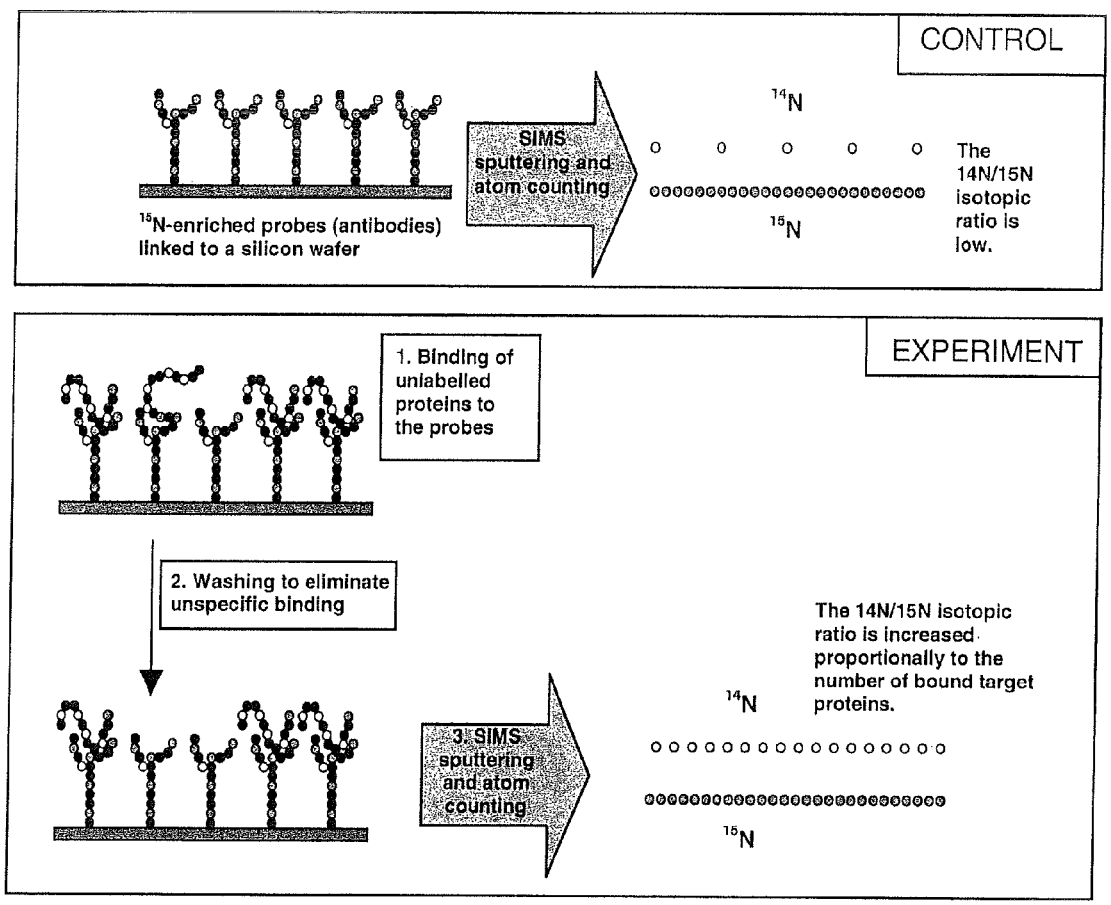
FIG. 1: Schematic illustration of the principle of SIMS detection of the binding of probes to their target proteins. The biomolecules (probes and targets) are fragmented down to the atomic level (dynamic SIMS conditions). Hence, each individual couple of probe/target gives hundreds of $^{15}$N and $^{14}$N atoms (in the form of CN⁻ molecular secondary ions in a real experiment), which are easily counted in the SIMS analyser (amplification). The measurement of the increase in the $^{14}$N/$^{15}$N isotopic ratio allows the quantification of those target proteins bound to antibodies.

The term "nucleic acid" as used herein means a polymer composed of nucleotides, e.g., deoxyribonucleotides or ribonucleotides, or compounds produced synthetically such as PNA which can hybridize with naturally occurring nucleic acids in a sequence specific manner analogous to that of two naturally occurring nucleic acids, e.g., can participate in Watson-Crick base-pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g. wherein one or more of the hydroxyl groups are replaced with halogen atoms or aliphatic groups, or are functionalized as ethers, amines, or the like.

The term "protein" as used herein means a polymer of amino acid residues linked together by peptide bonds. The term, as used herein, refers to proteins, polypeptides, and peptides of any size, structure, or function. Typically, however, a protein will be at least six amino acids long. Preferably, if the protein is a short peptide, it will be at least about 10 amino acid residues long. A protein may be naturally occurring, recombinant, or synthetic, or any combination of these. A protein may also be just a fragment of a naturally occurring protein or peptide. A protein may be a single molecule or may be a multi-molecular complex. The term protein may also apply to amino acid polymers in which one or more amino acid residues are an artificial chemical analogue of a corresponding naturally occurring amino acid. An amino acid polymer in which one or more amino acid residues is an "unnatural" amino acid, not corresponding to any naturally occurring amino acid, is also encompassed by the use of the term "protein" herein.

The phrase "oligonucleotide bound to a surface of a solid support" refers to an oligonucleotide or mimetic thereof, such as PNA, that is immobilized on a surface of a solid substrate in a spot, where the substrate can have a variety of configurations, e.g. a sheet, bead, or other structure. In certain embodiments, the collections of features of oligonucleotides employed herein are present on a surface of the same planar support, e.g. in the form of an array.

The term "array" encompasses the term "microarray" and "nanoarray". Arrays, as described in greater detail below, are generally made up of a number of distinct or different probes bound to the surface of a solid support, also referred to as substrate-immobilized probes. In one embodiment, the array of the invention is a homoarray, in which the array of the invention comprises probes of only-one chemical type, i.e. only nucleic acid probes or only peptide or protein probes, etc. In another embodiment, the array of the invention is a heteroarray, in which the array of the invention comprises a mixture of types of probes, such as a mixture of nucleic acid probes and protein probes.

The term "nanowell" applies to an area of nanometer dimensions in which probes are bound. The term "microwell" applies to an area of micrometer dimensions in which probes are bound.

The term "NanoArrayDevice" or NAD applies to a feature (which may exist in many identical copies or different forms on a single chip) of micrometer dimensions. A NAD may comprise a set of nanowells or just a set of discrete areas (without wells but containing probes) that may themselves be or not be within a microwell.

The term "common secondary ions" refers to those ions that are generated and analyzed in SIMS and that do NOT contain the rare, stable (or unstable) isotopes of their constituent elements. Examples of common secondary ions include $^{12}$C$^{14}$N⁻, $^{12}$C⁻ etc.

The term "rare secondary ions" refers to those ions that are generated and analyzed in SIMS and that DO contain at least one of the rare, stable (or unstable) isotopes of their constituent elements in the proportions used in the labeling of the probes and/or target molecules. Examples of rare secondary ions include $^{13}$C⁻, $^{13}$C$^{14}$N⁻, $^{12}$C$^{15}$N⁻, and $^{13}$C$^{15}$N⁻.

The term "background common secondary ions" refers to those ions that are generated and analyzed in SIMS and that contain the rare, stable (or unstable) isotopes of their constituent elements in the naturally occurring proportions (as opposed to the proportions used in the labeling of the probes and/or target molecules). Examples of natural secondary ions in their natural proportions include $^{12}C^-$, $^{13}C^{14}N^-$, $^{12}C^{15}N^-$ and $^{13}C^{15}N^-$ in the proportions 0.98538:0.01096:0.00362: 0.00004.

Figure 2:
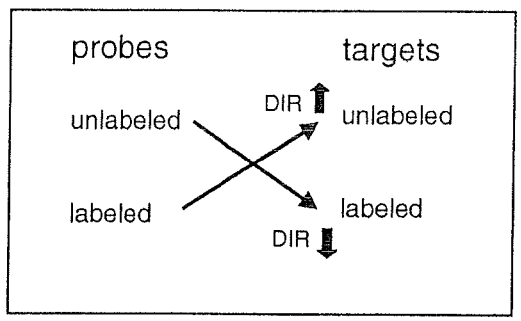
FIG. 2: increase or decrease in the DIR depending on whether the probe or the target is labeled.

The term "Detection Isotopic Ratio", or DIR, as applied to a discrete area or microwell or nanowell refers to the ratio of the number of the common secondary ions to the sum of the numbers of common plus at least one of the rare secondary ions obtained by SIMS or by related methods (e.g. $^{12}C^{14}N^-/(^{12}C^{14}N^-+^{12}C^{15}N^-)$ or $^{12}C^{14}N^-/^{12}C^{14}N^-+^{13}C^{14}N^-)$ or $^{12}C^{14}N^-/(^{12}C^{14}N^-+^{12}C^{15}N^-+^{13}C^{14}N^-)$ or $^{12}C^{14}N^-/(^{12}C^{14}N^-+^{12}C^{15}N^-+^{13}C^{14}N^-+^{13}C^{15}N^-)$ or $^{12}C^-/(^{12}C^-+^{13}C^-)$, etc.). FIG. 2 shows the increase or decrease in the DIR depending on whether the probe or the target is labeled. (If both probe and target are labeled with, for example, different isotopes, the direction of change in the DIR must be worked out for each particular case).

The term "exogenous isotope" refers to those isotopes that are not naturally contained in the biomolecules (probes and targets) but that have been added to these molecules by the user. The exogenous isotopes may be covalently linked to the biomolecules via standard chemistry or biochemistry. Alternatively, the exogenous isotopes may be covalently attached to a molecule that itself interacts strongly with either the probe or the target and that does not reduce significantly recognition of targets by probes. Examples of exogenous isotopes include: $^{79}Br$ and $^{81}Br$.

The term "reference discrete area" refers to discrete areas, microwells or nanowells wherein probes (labeled or unlabeled) are not put into contact with the sample to be tested, or wherein there is no specific interaction between probe and target (i.e. the target is not present in the sample to be analyzed).

THE INVENTION

Nature of Supporting Material and Surface

One object of the invention is an array comprising a substantially planar substrate having a conducting surface and a number of discrete areas, which may or may not be in the form of wells, containing probes being labeled with at least one rare isotope (e.g. stable heavy or light isotope or unstable isotope) or with at least one exogenous isotope (e.g. $^{79}Br$, $^{81}Br$).

According to the invention, a substantially planar substrate having a conducting surface is a silicon wafer or any other solid or semi-solid surface made of gold, silver, aluminum, copper, platinum, palladium or other metal, or semiconductors such as GaAs, InP, or other material treated to make the surface conducting e.g. polymer material, polymer-coated material, superconducting material, ceramics, metal oxides, silicon oxide, etc.

In one embodiment of the invention, said substantially planar substrate having a conducting surface is compatible with SIMS.

In a preferred embodiment of the invention, said SIMS-compatible substantially planar substrate having a conducting surface is a silicon wafer.

Discrete Areas that are in the Form of Microwells

Another object of the invention is a microwell array being the microarray as described here above, wherein the discrete areas are microwells that contain probes labeled with at least one rare, stable or unstable isotope. The microwells may be any shape, for example dots, lines, circles, squares or triangles, and may be arranged in any larger pattern, for example rows and columns, lattices, grids etc. These microwells contain probes labeled with at least one rare, stable or unstable isotope.

In one embodiment of the invention, the microwell array of the invention comprises from 10 to 100000 microwells, in another embodiment from 10 to 25000 microwells, in another embodiment from 100 to 10000 microwells and in another embodiment from 1000 to 5000 microwells.

In one embodiment of the invention, the shape and the size of the microwells are suitably determined to store a single cell in each microwell.

In one embodiment, each microwell has one of the dimensions length, width or diameter in the range from 1 μm to 1000 μm, in another embodiment from 1 μm to 500 μm, in another embodiment from 1 μm to 200 μm and in another embodiment from 1 to 100 μm.

In one embodiment, each microwell has a depth from 1 μm to 100 μm, in another embodiment from 1 μm to 50 μm, in another embodiment from 5 μm to 20 μm.

The distance between each microwell may be from 25 to 5000 μm, in another embodiment from 100 to 1000 μm and in another embodiment from 50 μm to 150 μm.

The microwell may be of any shape: for example it can be cylindrical, non-cylindrical such as a polyhedron with multiple faces (a parallelepiped, hexagonal column, octagonal column), an inverted cone, an inverted pyramid, or it may have a shape combining two or more of these shapes. For conical and parallelepiped shapes, the bottom of the microwell is normally flat, but curved surfaces (convex or concave) are also possible.

In one embodiment of the invention, the substantially planar conducting surface carrying the set of microwells may be shaped as a rectangular solid or a disc (although other shapes are possible), having a length of 1 cm, a width of 1 cm and a thickness of about 250 μm.

Discrete Areas in the Form of Nanowells

Another object of the invention is a nanowell array being the nanoarray as described here above, wherein the discrete areas are nanowells that contain probes being labeled with at least one rare, stable or unstable isotope. The nanowells may be any shape, for example dots, lines, circles, squares or triangles, and may be arranged in any larger pattern, for example rows and columns, lattices, grids etc. These nanowells contain probes labeled with at least one rare, stable or unstable isotope.

In one embodiment of the invention, the nanowell array of the invention comprises from 10 to 100000 nanowells, in another embodiment from 10 to 25000 nanowells, in another embodiment from 100 to 10000 nanowells and in another embodiment from 1000 to 5000 nanowells.

In one embodiment, each nanowell has one of the dimensions length, width or diameter being from 1 nm to 1000 nm, in another embodiment from 5 nm to 500 nm, in another embodiment from 10 nm to 200 nm and in another embodiment from 50 to 100 nm.

In one embodiment, each nanowell has a depth from 1 nm to 100 nm, in another embodiment from 1 nm to 50 nm, in another embodiment from 5 nm to 20 nm.

The distance between each nanowell may be from 10 to 1000 nm, in another embodiment from 50 to 500 nm and in another embodiment from 100 nm to 200 nm.

The nanowell may be of any shape: for example it can be cylindrical, noncylindrical such as a polyhedron with multiple faces (a parallelepiped, hexagonal column, octagonal column), an inverted cone, an inverted pyramid, or it may have a shape combining two or more of these shapes. For conical and parallelepiped shapes, the bottom of the nanowell is normally flat, but curved surfaces (convex or concave) are also possible.

In one embodiment of the invention, the substantially planar conducting surface carrying the set of nanowells may be shaped as a rectangular solid or a disc (although other shapes are possible), having a length of 1 cm, a width of 1 cm and a thickness of about 250 µm.

Discrete Areas that are not in the Form of Wells

Another object of the invention is an array being an arrangement of a set of discrete areas, or pattern units, forming a larger pattern on a substrate. The discrete areas or pattern units may be any shape, for example dots, lines, circles, squares or triangles, and may be arranged in any larger pattern, for example rows and columns, lattices, grids etc. These discrete areas contain probes labeled with at least one rare, stable (or unstable) isotope.

In one embodiment of the invention, the array of the invention comprises from 10 to 100000 discrete areas, in another embodiment from 10 to 25000 discrete areas, in another embodiment from 100 to 10000 discrete areas and in another embodiment from 1000 to 5000 discrete areas.

In one embodiment of the invention, the array of the invention is a microarray. In this embodiment, each discrete area has one of the dimensions length, width or diameter being from 1 µm to 1000 µm, in another embodiment from 5 µm to 500 µm, in another embodiment from 10 µm to 200 µm and in another embodiment from 50 to 100 µm. The distance between each discrete area may be from 10 to 1000 µm, in another embodiment from 50 to 500 µm and in another embodiment from 100 µm to 200 µm.

In one embodiment of the invention, the array of the invention is a nanoarray. In this embodiment each discrete area has one of the dimensions length, width or diameter being from 1 nm to 1000 nm, in another embodiment from 5 nm to 500 nm, in another embodiment from 10 nm to 200 nm and in another embodiment from 50 nm to 100 nm. The distance between each discrete area may be from 10 to 1000 nm, in another embodiment from 50 nm to 500 nm and in another embodiment from 100 µm to 200 nm.

In one embodiment of the invention, the membrane or silicon wafer carrying the set(s) of discrete areas may be shaped as a rectangular solid or a disc (although other shapes are possible), having for example a length of 1 cm, a width of 1 cm and a thickness of about 250 µm.

Probes

Chemical Nature and Isotopic Composition of Probes

In this embodiment, the probes, which bind to targets (usually the biomolecules that constitute cells but even viruses, organelles or cells themselves), may be made of any molecules (biological or non-biological) such as nucleic acids (oligonucleotides, DNA, RNA, PNA), peptides or proteins (antibodies, enzymes), ligands (an antigen, enzyme substrate, receptor or ligand for the receptor), glycans, lipids, polyamines, phages, viruses, or combination of these molecules.

According to the invention, the probes contain at least one rare, stable or unstable isotope:

in one embodiment, probes contain at least one heavy stable isotope such as $^2H$, $^{13}C$, $^{15}N$, $^{17}O$, $^{18}O$, $^{33}S$, $^{34}S$ and $^{36}S$.

in another embodiment, probes contain at least one unstable isotope such as $^3H$ and $^{14}C$, in another embodiment, probes contain at least one exogenous isotope such as $^{79}Br$ and $^{81}Br$.

Attachment or Grafting of Probes

The attachment or grafting of probes to the array is achieved by techniques well-known in the art. The probes may be adsorbed, physisorbed, chemisorbed, or covalently attached to the arrays. Lithography printing may also be used to allow probes to be transferred and adsorbed directly or indirectly to surfaces in a patterned fashion.

For example, attachment of probes may be achieved by introducing functional groups onto the surface for chemical reaction between the surface and the probe to be grafted.

The carboxyl group (COOH) is one of the best-known functional groups for grafting. Chemical bonds are produced between amino-groups from proteins and carboxyl functional groups. Acrylic acid or copolymerised vinylsilane and maleic anhydride acid can also be used to generate silicon-COOH substrates that act as spacers to graft proteins onto the surface using e.g. 1-ethyl-3-(3-dimethylaminopropyl) carbodiimide hydrochloride.

Identification of Probes

In one embodiment in which a diversity of different probes is attached to the array, the probes are identified via the position or coordinates of the discrete area containing the probes.

Nature and Origin of Samples

According to the method of the invention, the sample to be tested may be isolated from cells, tissue, organ, body fluid such as for instance sera, plasma, seminal fluid, synovial fluid, cerebrospinal fluid, blood or urine, a cell culture, water such as sewage water, freshwater, marine coastal water, ground water . . . .

According to the method of the invention, the sample to be tested may comprise nucleic acids (oligonucleotides, DNA, RNA, PNA), peptides or proteins (antibodies, enzymes), ligand (an antigen, enzyme substrate, receptor or ligand for the receptor), glycans, lipids, polyamines, phages, viruses or a combination thereof. Thus the biomolecules to be detected may be nucleic acids (oligonucleotides, DNA, RNA, PNA), peptides or proteins (antibodies, enzymes, prions), ligand (an antigen, enzyme substrate, receptor or ligand for the receptor), glycans, lipids, polyamines, phages, viruses or a combination thereof.

Labeling of Probes

According to the method of the invention, the probes or the targets, i.e. the biomolecules present in the sample(s) to be tested, are labeled with rare, stable or unstable isotopes or exogenous isotopes.

In one embodiment, probes or targets may be labeled with at least one rare, stable isotope such as $^2H$, $^{13}C$, $^{15}N$, $^{17}O$, $^{18}O$, $^{33}S$, $^{34}S$ and $^{36}S$.

In another embodiment, probes or targets may be labeled with at least one unstable isotope such as $^3H$ and $^{14}C$.

In another embodiment, probes or targets may be labeled with at least one exogenous isotope such as $^{79}Br$ and $^{81}Br$.

Labeled probes can be obtained by two techniques, in vivo and in vitro:

In the case of in vitro labeling, 1) the polymerase chain reaction is used to produce labeled oligonucleotides, 2) peptide synthesis is used to produce labeled peptides, 3) in vitro transcription/translation is used to produce labeled RNA and labeled proteins, 4) reverse transcription is used to produce labeled cDNA, 5) chemical synthesis is used to produce labeled PNA.

In the case of in vivo labeling, either prokaryotic or eukaryotic cells are grown on media containing nutrients (such as $NH_4Cl$, glucose and amino acids) labeled with combinations of $^2H$, $^{13}C$, $^{15}N$, $^{17}O$, $^{18}O$, $^{33}S$, $^{34}S$ and $^{36}S$ or with combinations of $^3H$, $^{14}C$, or other unstable isotopes with long half-lives. These cells thus produce labeled probes (such as antibodies or bacteriophage or nucleic acids or proteins or sugars or other cellular constituents).

Where the targets, i.e. the biomolecules present in the sample(s) to be tested, are to be labeled, the cells are generally grown on media containing nutrients (such as $NH_4Cl$, glucose and amino acids) labeled with combinations of $^2H$, $^{13}C$, $^{15}N$, $^{17}O$, $^{18}O$, $^{33}S$, $^{34}S$ and $^{36}S$ or with combinations of $^3H$ and $^{14}C$. These cells thus produce labeled biomolecules.

Contact Between Sample and Array

In one embodiment of the method of the invention, the sample to be tested is put in contact with the array (microarray or nanoarray) containing a number of diverse probes.

In another embodiment, where a number of samples is to be tested, each sample is put in contact with one or more microwells of a microwell array.

In another embodiment, where the number and diversity of samples to be tested corresponds to the number and diversity of single cells, the contents of each single cell, obtained via an appropriate method, is put into contact with one microwell of a microwell array.

Conditions of Interaction Between Probe and Target

The sample(s) is/are then contacted with the array under conditions that allow the probes present onto the array to interact with the target biomolecules.

The binding of probes to their targets is then performed in a variety of buffers from which, typically, the common $^{12}C$ and $^{14}N$ isotopes are absent (such as Phosphate Buffered Saline). After careful washing with pure water (preferably at low temperature to limit the dissociation of probes from their targets) to eliminate salts (which can form crystals at the drying step), the unbound molecules and the big cellular debris, the array is dried in a dust-free atmosphere either in an oven under vacuum or by freeze-drying.

Detection by SIMS and Other Related Techniques

According to the method of the invention, counting the numbers of rare and common secondary ions so as to obtain the Detection Isotopic Ratio allows detection of the duplexes probe/target.

In one embodiment, the duplexes probe/target are detected by Dynamic Secondary Ion Mass Spectrometry (D-SIMS). In another embodiment, the duplexes probe/target are detected by Time-of-Flight Secondary Ion Mass Spectrometry (TOF-SIMS).

Secondary Ion Mass Spectrometry (SIMS) allows the analysis of the surface composition of inorganic and organic materials based on mass spectral analysis of secondary ions extracted from the surface (1 nm-1 μm depth) of a solid sample under the impact of an energetic beam of primary ions. Molecules are fragmented by the primary ion beam in D-SIMS either totally into their constituent atoms by dynamic D-SIMS or partially into molecular fragments such as amino acids by ToF-SIMS. SIMS-related technologies such as Laser SNMS may also be used to detect probe/target interactions.

In one embodiment of the method of the invention, the probes that are attached to the array are labeled with rare, stable or unstable isotopes or exogenous isotopes. In this embodiment, the sample(s) to be tested have biomolecules (targets) that only contain these rare isotopes in their natural proportions (or even lower than these proportions).

The presence of an interaction probe/target is determined by the comparison of the Detection Isotopic Ratio obtained from each discrete area, microwell or nanowell to the background Detection Isotopic Ratio obtained from the reference discrete area, microwell or nanowell or from discrete areas in which there is no specific interaction between labeled probe and target (i.e. the target is not present in the sample to be analyzed) or in which there is a specific interaction between unlabeled probe and unlabeled target.

Therefore, in the case where probes are labeled and targets are unlabeled, the presence of an interaction probe/target is revealed if the Detection Isotopic Ratio obtained from one discrete area, microwell or nanowell is significantly superior to the Detection Isotopic Ratio obtained from the reference discrete area, microwell or nanowell. For example, in the case where probes are labeled with $^{13}C$, the presence of an interaction probe/target is revealed if the Detection Isotopic Ratio of $^{12}C/(^{12}C+^{13}C)$ (or alternatively $^{12}C^{14}N/(^{12}C^{14}N+^{12}C^{15}N)$) obtained from one discrete area, microwell or nanowell is superior to the Detection Isotopic Ratio obtained from the reference discrete area, microwell or nanowell, for the same instrumental settings.

Therefore, in the case where probes are unlabeled and targets are labeled, the presence of an interaction probe/target is revealed if the Detection Isotopic Ratio obtained from one discrete area, microwell or nanowell is significantly inferior to the Detection Isotopic Ratio obtained from the reference discrete area, microwell or nanowell. For example, in the case where probes are labeled with $^{13}C$, the presence of an interaction probe/target is revealed if the ratio of $^{12}C/(^{12}C+^{13}C)$ secondary ions (or alternatively $^{12}C^{14}N/(^{12}C^{14}N+^{12}C^{15}N)$) obtained from one discrete area, microwell or nanowell is inferior to this ratio of secondary ions obtained from the reference discrete area, microwell or nanowell, for the same instrumental settings.

Therefore, in the case where both probes and targets are labeled with the same isotope/isotopes, the presence of an interaction probe/target is revealed if the Detection Isotopic Ratio obtained from one discrete area, microwell or nanowell is significantly different from the Detection Isotopic Ratio obtained from the reference discrete area, microwell or nanowell.

According to the invention, the probes or targets may also be labeled with more than one rare, stable or unstable isotopes or exogenous isotopes of their constituent elements. For example, probes or targets may be labeled with $^{13}C$ and $^{15}N$. Multiple labeling such as $^{13}C^{15}N$ of the probes is particularly useful to minimize the background.

According to the invention, where the targets are labeled with rare, stable (or unstable) isotopes, various experimental conditions (for example, with and without drug treatments) may be differentiated by a differential labeling of each condition.

The Method of Detection and Quantification

One object of the invention is a method for detecting and quantifying in at least one sample the presence or absence of at least one biomolecule, comprising:
  (a) putting at least one of said samples into contact with an array under conditions that allow the probes present on the array to interact with the target biomolecules, the probes present on the array or the biomolecules present in the sample being labeled with at least one rare, stable (or unstable) isotope,
  (b) washing and drying the array,
  (c) detecting and counting by SIMS the common secondary ions along with the corresponding rare secondary ions.

This allows the determination of the DIR.

The DIR obtained from each discrete area, microwell or nanowell is then compared to the DIR obtained from the reference discrete area, microwell or nanowell; a significant change of the DIR (see FIG. 2) is an evidence for the presence (detection) of an interaction probe/target. Moreover, the precise determination of the DIR allows quantifying the number of interactions between probe and target. The precise determination of the DIR is obtained after sputtering the maximum quantity of material so as to obtain good counting statistics of both the common and the rare secondary ions. To calculate the number of targets interacting with the probes per discrete area (microwell or nanowell or indeed a sample unit area within the discrete area) it is necessary to know: a) the density of the probes on the surface of the discrete area and b) the number of atoms of each isotope of interest in the both individual probe and individual target. This knowledge then allows the DIR to be plotted as a function of the number of targets per discrete area.

APPLICATIONS OF THE INVENTION

According to another embodiment, said method for detecting and quantifying in at least one sample the presence or absence of at least one biomolecule, allows the determination of a molecular atlas of said sample, which means the determination of the transcriptome, proteome, lipidome, metabolome, glycome or interactome of said sample, or allows the determination of biomolecules and their interactions in a single cell.

Application to Molecular Atlas

According to one embodiment of the invention, the method for detecting and quantifying in a sample the presence or absence of at least one biomolecule, is intended for providing a molecular atlas of said sample.

In one embodiment, the diversity of biomolecules to be detected and quantified is genomic sequences, allowing the determination of genomic variation in said sample.

In another embodiment, the diversity of biomolecules to be detected and quantified is RNA, allowing the determination of the transcriptome of said sample.

In another embodiment, the diversity of biomolecules to be detected and quantified is proteins, allowing the determination of the proteome of said sample.

In another embodiment, the diversity of biomolecules to be detected and quantified is lipids, allowing the determination of the lipidome of said sample.

In another embodiment, the diversity of biomolecules to be detected and quantified is metabolites, allowing the determination of the metabolome of said sample.

In another embodiment, the diversity of biomolecules to be detected and quantified is glycosylated proteins, allowing the determination of the glycome of said sample.

In another embodiment, the diversity of biomolecules to be detected and quantified is proteins that interact with at least one specific probe, allowing the determination of the interactome of said sample.

Application to Single Cell

According to another embodiment of the invention, the method for detecting and quantifying at a single cell level the presence or absence of at least one biomolecule, is intended for providing a molecular atlas of a single cell level.

In one embodiment, the diversity of biomolecules to be detected and quantified is genomic sequences, allowing the determination of genomic variation at the single cell level.

In another embodiment, the diversity of biomolecules to be detected and quantified is RNA, allowing the determination of the transcriptome at the single cell level.

In another embodiment, the diversity of biomolecules to be detected and quantified is proteins, allowing the determination of the proteome at the single cell level.

In another embodiment, the diversity of biomolecules to be detected and quantified is lipids, allowing the determination of the lipidome at the single cell level.

In another embodiment, the diversity of biomolecules to be detected and quantified is metabolites, allowing the determination of the metabolome at the single cell level.

In another embodiment, the diversity of biomolecules to be detected and quantified is glycosylated proteins, allowing the determination of the glycome at the single cell level.

In another embodiment, the diversity of biomolecules to be detected and quantified is proteins that interact with at least one specific probe, allowing the determination of the interactome at the single cell level.

Application to Disease

Another object of the invention is the use of said method for detecting and quantifying at least one biomolecule in a sample or at a single cell level for:

predicting a predisposition to a disease, or for diagnosing a disease in a subject, screening therapeutic agents, monitoring the efficacy of a therapeutic agent administrated to a subject in order to treat a disease.

Another object of the invention is a method for predicting a predisposition to a disease, or for diagnosing a disease in a subject. This comprises:

(a) putting at least one sample isolated from said subject in contact with an array under conditions that allow the probes present onto the array to interact with the target biomolecules known to be associated with or differentially expressed in said disease, the probes present on the array being labelled with at least one rare, stable (or unstable) isotope, (b) washing and drying the array, (c) detecting and counting by SIMS the common secondary ions along with the corresponding rare secondary ions, wherein the number of interactions between probe and target is quantified by the comparison of the DIR obtained from each discrete area, microwell or nanowell to the DIR obtained from the reference discrete area, microwell or nanowell or from discrete areas in which there is no specific interaction between probe and target (i.e. the target is not present in the sample to be analyzed) or in which there is a specific interaction between unlabeled probe and unlabeled target, (d) comparing said pattern of expression to a standard pattern, wherein the presence/absence or the increase/decrease of said at least one biomolecule known to be associated with or differentially expressed in said disease is indicative of a likelihood to develop a disease or of the presence of a disease.

In one embodiment, the subject is a mammal. In a preferred embodiment, the subject is a human being.

According to the method of the invention, the sample to be tested may be isolated from cells, tissue, organ, or body fluid such as for instance sera, plasma, seminal fluid, synovial fluid, cerebrospinal fluid, blood or urine, from the subject.

The sample may be derived from diseased cells or tissues. For example, the cells or tissues may be infected by a pathogen such as HIV, influenza, malaria, hepatitis, cytomegalovirus, herpes simplex virus. In one embodiment, the cells or tissues are infected by a viral or a bacterial pathogen. In another embodiment, the disease is cancer. In another embodiment, the disease is a neurodegenerative disease such as Parkinson, Alzheimer or Multiple Sclerosis.

In one embodiment of the invention, said method is intended to predict a predisposition to a cancer, or for diagnosing a cancer in a subject.

In another embodiment of the invention, said method is intended to predict a predisposition or to diagnose a bacterial disease.

In another embodiment of the invention, said method is intended to predict a predisposition or to diagnose a viral disease.

Another object of the invention is a method for screening therapeutic agents, comprising:
(a) cultivating cells with at least one therapeutic agent of interest,
(b) putting at least one sample isolated from said culture in contact with an array under conditions that allow the probes present onto the array to interact with the target biomolecules, the probes present on the array being labelled with at least one heavy or unstable isotope,
(c) washing and drying the array,
(d) detecting and counting by SIMS the common secondary ions along with the corresponding rare secondary ions, wherein the number of interactions between probe and target is quantified by the comparison of the DIR obtained from each discrete area, microwell or nanowell to the DIR obtained from the reference discrete area, microwell or nanowell or from discrete areas in which there is no specific interaction between probe and target (i.e. the target is not present in the sample to be analyzed) or in which there is a specific interaction between unlabeled probe and unlabeled target,
(e) comparing said pattern of expression to a standard pattern, wherein the increase or decrease of certain biomolecules is indicative of the efficacy of said therapeutic agent.

Another object of the invention is a method for monitoring efficacy of a therapeutic agent administrated to a subject to treat a disease, said method comprising:
(a) putting at least one sample isolated from said subject in contact with an array under conditions that allow the probes present onto the array to interact with the target biomolecules, the probes present on the array being labelled with at least one heavy or unstable isotope,
(b) washing and drying the array,
(c) detecting and counting by SIMS the common secondary ions along with the corresponding rare secondary ions, wherein the number of interactions between probe and target is quantified by the comparison of the DIR obtained from each discrete area, microwell or nanowell to the DIR obtained from the reference discrete area, microwell or nanowell or from discrete areas in which there is no specific interaction between probe and target (i.e. the target is not present in the sample to be analyzed) or in which there is a specific interaction between unlabeled probe and unlabeled target,
(d) obtaining a pattern of expression from said sample of at least one biomolecule at different times during the treatment of the subject,
(e) comparing said patterns of expression to a standard pattern, wherein the increase or decrease of said biomolecules known to be associated with or differentially expressed in said disease is indicative of the efficacy of said therapeutic agent for treating the subject.

EXAMPLES

In the following description, all experiments for which no detailed protocol is given are performed according to standard protocol.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Experiment 1

This experiment shows that the SIMS technique allows a quantitative detection of the proportion of the $^{13}$C isotope in a mixture containing isotopically labeled proteins and a different amount of unlabeled molecules.

Isotopic Labeling and Dilution

Isotope-labeled molecules are generally supplied in a buffer containing protectants and preservatives such as glycerol (a source of $^{12}$C) and sodium azide (a source of $^{14}$N). These agents are used to preserve dialysis membranes (as supplied by Millipore). The aim of the following experiments is to determine the conditions of dialysis needed to remove them.

Figure 3:
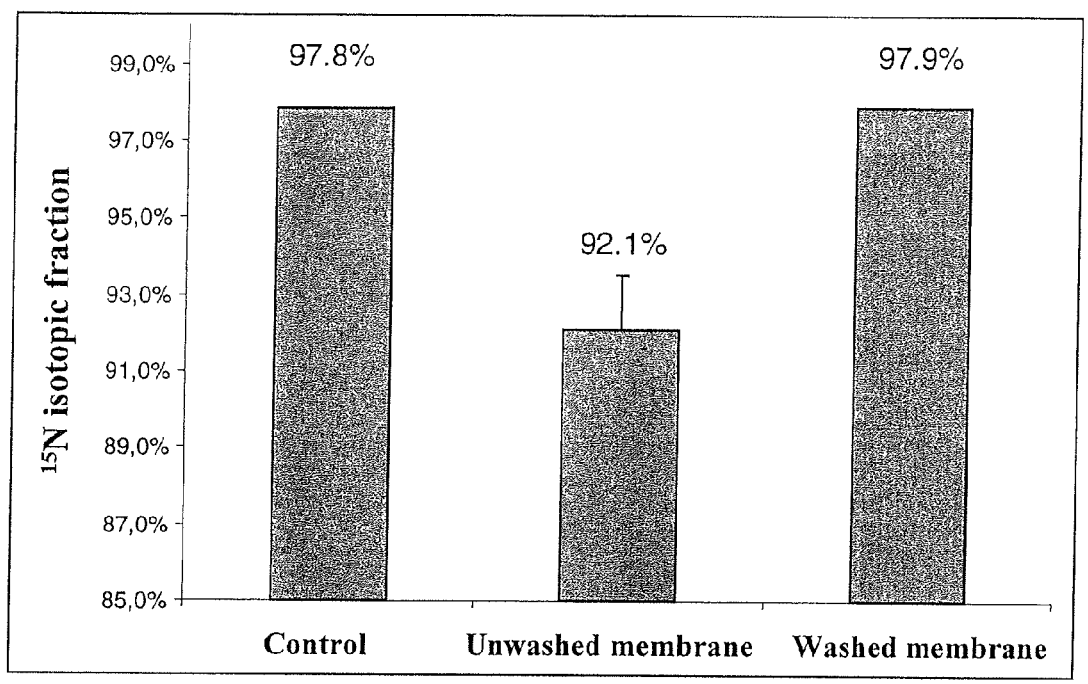
FIG. 3: isotopic fraction of $^{15}$N.

Proteins were extracted from *E. coli* grown in a minimal medium in which the only available nitrogen was $^{15}$N. Using SIMS, the isotopic fraction of these proteins was found to be 97.8%±0.02%. 20 µg of these labeled proteins were dialysed for 6 hours in water on Millipore dialysis membranes which either were unwashed or had been washed previously. FIG. 3 shows the isotopic fraction of $^{15}$N in the dialyzed solutions.

The level of the isotopic fraction of the washed membrane was similar to that of the control (97.9%±0.02%) whilst that of the unwashed membrane (containing contaminant nitrogen) was lower (92.1%±1.4%). Hence, prewashing the dialysis membrane restored the initial isotopic fraction.

Figure 4:
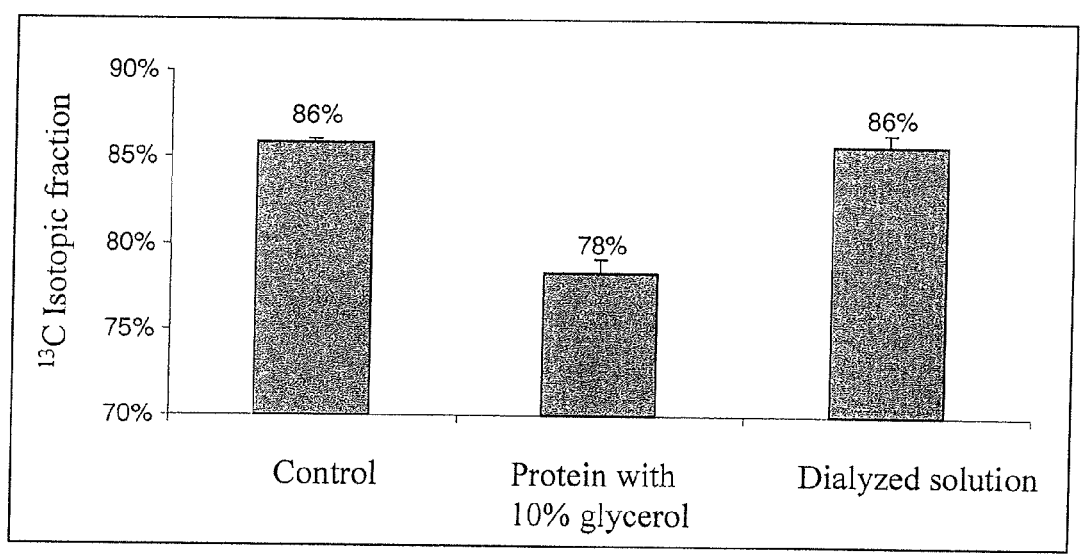
FIG. 4: isotopic fraction of $^{13}$C.

Proteins were also extracted from bacteria grown in a medium in which the only available carbon was $^{13}$C. The isotopic fraction of these proteins as measured by SIMS was 86%±0.5%. These proteins were then dissolved in water and a second solution of them was made to a final concentration of 10% glycerol. FIG. 4 shows the isotopic fraction of $^{13}$C in these solutions.

The addition of glycerol reduced the isotopic fraction to 78%±2% but the initial fraction (86%±2%) was recovered by the subsequent dialysis which eliminated the glycerol.

Experiment 2

This experiment shows that the isotopically labeled oligonucleotide (probes) can be prepared using the PCR technique and an unconventional buffer that does not contain nitrogen compounds (which, as contaminants, might perturb the DIR measurement described in the section "Definitions").

Use of a Borax Buffer to Reduce Nitrogen Contamination

Introduction

Many methods in biology use Tris-based buffers. This organic molecule is an excellent buffer and, moreover, does not lead to the precipitation of calcium or magnesium salts. For our method, however, Tris has the disadvantage of containing $^{14}$N and of having a strong affinity for DNA (and other macromolecules). This disadvantage arises because this $^{14}$N is an important contaminant in our method which depends on measuring accurately the $^{15}N/(^{14}N+^{15}N)$ ratio resulting from the hybridization of a $^{15}N$ probe with a $^{14}N$ target.

The two approaches to making DNA without contaminant nitrogen are either i) using Tris in the buffers and then removing it once the DNA has been made or ii) using Tris-free buffers. Since the first method entails purification methods that are time-consuming, wasteful and expensive, we adopted the second solution to provide the right pH and concentration conditions for PCR (polymerase chain reaction). Although, to our knowledge, no literature describes the use of borax buffers for PCR, we used a borax buffer, an inorganic buffer that does not contain nitrogen and that maintains the same pH values as Tris buffers.

Material and Methods
PCR Method

| chemicals | C init | volume | C final |
| --- | --- | --- | --- |
| Borax Buffer | 0.08 M | 12.5 | 20 mM |
| KCl | 1 M | 2.5 | 50 mM |
| MgCl2 | 25 mM | 4 | 2 mM |
| dNTP | 10 mM | 2 | 0.8 mM |
| Taq Polymerase | 1 U/µL | 2.5 | 0.05 U/µL |
| Primer S | 100 µM | 0.5 | 1 µM |
| Primer AS | 100 µM | 0.5 | 1 µM |
| DNA Sample | — | 1 | 25 |
| Water | — | 24.5 | |
| Total | | 50 | |

A 200 bp sequence of DNA from the PML gene was amplified. The template itself was made using only one round of amplification (to avoid error generation). Either 20 cycles of PCR were performed to determine quantitatively the effect of the borax buffer (and limit error generation) or 60 cycles were performed to consume the limiting substrate and obtain maximal amplification. The amplicons were analyzed by electrophoresis on 1% agarose gels. The results below are shown for a Tris buffer and for a borax buffer.

Results

In the case of 20 cycles of amplification, the borax buffer gives half the yield of the Tris buffer and, significantly, the borax buffer did not generate amplicons of different sizes. This means that the polymerase continued replication to the end of the templates. In the case of 60 cycles of amplification, both Tris and borax buffers gave similar results.

Conclusion

A borax buffer is perfectly suitable for reactions such as PCR amplification and hence for the synthesis of oligonucleotide probes. Hence this buffer can be used to avoid contaminant nitrogen as required in the SIMS analyses proposed here.

Experiment 3

The inventors are currently preparing DNA and protein arrays for detection by SIMS. Isotopically labeled and unlabeled nucleotide probes have been prepared using PCR to hybridize with DNA containing part of the PML gene (which encodes the Promyelocytic Leukemia protein). Probe sequence (length 298 bases) was: TGTCTCCAAT ACAAC-GACAG CCCAGAAGAG GAAGTGCAGC CAGAC-CCAGT GCCCCAGGAA GGTCATCAAG ATG-GAGTCTG AGGAGGGGAA GGAGGCAAGG TTGGCTCGGA GCTCCCCGGA GCAGCCCAGG CCCAGCACCT CCAAGGCAGT CTCACCACCC CAC-CTGGATG GACCGCCTAG CCCCAGGAGC CCCGT-CATAG GAAGTGAGGT CTTCCTGCCC AACAG-CAACC ACGTGGCCAG TGGCGCCGGG GAGGCAGAGG AACGCGTTGT GGTGATCAGC AGCTCGGAAG ACTCAGAT (SEQ ID NO: 1).

The primers were: (forward) 5'-TGTCTCCAATACAAC-GACAGC-3' (SEQ ID NO: 2), (reverse) 5'-ATCTGAGTCT-TCCGAGCTGCT-3' (SEQ ID NO: 3).

These nucleotide probes are being covalently linked to silicon wafers using appropriate chemical techniques. This entails the following steps:

1) Cleaning the silicon wafer with a "piranha" mixture ($H_2O_2:H_2SO_4$ 1:3) to give an oxidized Si surface containing a high concentration of surface hydroxyl groups.
2) Coupling the surface hydroxyl groups to functional (e.g. aldehyde terminated) trichloro- or trialkyloxysilanes.
3) Attaching the nucleotide probes by putting them in contact with this functionalized surface.

Isotopically labeled and unlabeled antibody probes have been prepared. These included anti-CD34 and anti-clathrin. These antibody probes are being attached to silicon wafers by appropriate techniques. For example, we are first covering the surface of the wafer with protein A (which we have labeled isotopically, see below) and then adding the antibodies (to which protein A binds).

The gene encoding amino acids 32-327 of protein A from *Staphylococcus aureus* is cloned in a plasmid so as to create an N-terminal fusion with a Histidine tag (see sequence below). *Escherichia coli* BL21 (DE3) was transformed with this plasmid and was grown in minimal medium NG-5052 (see below for composition). 25 ml of a bacterial culture was grown in a 250 ml flask and shaken overnight (220 rpm) at 18° C. The culture was centrifuged (6000 g, 10 minutes at 4° C.) and the pellets were resuspended in 5 ml of buffer A (50 mM Na*PO4, 300 mM NaCl, pH 7.5). Lysozyme was added (final concentration 1 mg/ml) and the suspension was shaken for 30 minutes at room temperature before being sonicated (HD 2200/sonotronde MS72) twice for 30 seconds in pulses of 0.5 seconds at 20% of full power. The soluble and insoluble fractions of the lysate were then separated by centrifugation (20000 g 20 minutes at 4° C.). The supernatant was then added to an ion exchange column with nickel as counterion (Chelating HP 1 ml, GE Healthcare) previously equilibrated with 10 volumes of buffer A. The column was then washed with 20 volumes of buffer A followed by 10 volumes of buffer B (identical to buffer A except that it is at pH 6.5). The fusion protein, which binds to the column, was then eluted with 10 volumes of buffer C (identical to buffer A except that it is at pH 3). The eluate was analysed using SDS-PAGE with a gradient of acrylamide (7.5-16%) and the proteins were visualized using Coomassie Blue, silver nitrate and immuno-blotting with anti-His antibodies. The concentration of the fusion protein in the eluate was measured as 0.344 mg/ml (Bradford method) and the protein was 92% pure as determined by densitometry of the Coomassie Blue stained gel.

The fusion protein is now being labeled with $^{15}N$ using the above method of growth in N-5052 but using $^{15}N$-labeled ammonium chloride instead of unlabeled ammonium chloride.

Composition of Medium NG-5052

| | |
| --- | --- |
| $Na_2HPO_4$ | 50 mM |
| $KH_2PO_4$ | 50 mM |
| $NH_4Cl$ | 50 mM |

-continued

| | |
|---|---|
| Na$_2$SO$_4$ | 5 mM |
| MgSO$_4$ | 2 mM |
| Trace metals | 1x |
| Glycerol | 0.5% (w/v) |
| Glucose | 0.05% (w/v) |
| Kanamycin | 50 μg/ml |

Composition of Medium N-5052 (Studier et al., 2005 Protein Production by Auto-induction in High-density Shaking Cultures. *Protein Expression and Purification* 41: 207-234)

Medium NG-5052
Lactose 0.2% (w/v)

Composition of the "Trace Metals" Solution 5000×

| | |
|---|---|
| FeCl$_3$ | 50 mM |
| CaCl$_2$ | 20 mM |
| MnCl$_2$ | 10 mM |
| ZnSO$_4$ | 10 mM |

Sequence of the Protein A Fusion Protein:

(SEQ ID NO: 4)
MGSSHHHHHHSSGPAANAAQHDEAQQNAFYQVLNMPNLNADQRNGFIQS

LKDDPSQSANVLGEAQKLNDSQAPKADAQQNNFNKDQQSAFYEILNMPN

LNEAQRNGFIQSLKDDPSQSTNVLGEAKKLNESQAPKADNNFNKEQQNA

FYEILNMPNLNEEQRNGFIQSLKDDPSQSANLLSEAKKLNESQAPKADN

KFNKEQQNAFYEILHLPNLNEEQRNGFIQSLKDDPSQSANLLAEAKKLN

DAQAPKADNKFNKEQQNAFYEILHLPNLTEEQRNGFIQSLKDDPSVSKE

ILAEAKKLNDAQAPK

Probe-target association will be analyzed by SIMS and comparison will be made between SIMS technique and the standard fluorescence technique.

The invention claimed is:

1. A method for detecting and quantifying in at least one sample the presence or absence of at least one biomolecule, comprising:

(a) contacting said at least one sample with an array which comprises a substantially planar substrate having a conducting surface and a number of discrete areas containing probes being labeled with at least one rare, stable or unstable isotope or exogenous isotope;

(b) washing and drying the array;

(c) detecting and counting by dynamic secondary ion mass spectrometry (D-SIMS) the common secondary ions along with the corresponding rare secondary ions; and (d) detecting and quantifying in at least one sample the presence or absence of at least one biomolecule.

2. The method according to claim 1, wherein each sample to be tested is contacted with one or more discrete area of the array.

3. The method according to claim 1, wherein said sample to be tested is a single cell.

4. A method for determining a molecular atlas of at least one sample, wherein said molecular atlas is the determination of the transciptome, proteome, lipidome, metabolome, glycome and/or interactome of said at least one sample comprising:
(a) contacting said at least one sample with an array which comprises a substantially planar substrate having a conducting surface and a number of discrete areas containing probes being labeled with at least one rare, stable or unstable isotope or exogenous isotope;
(b) washing and drying the array;
(c) detecting and counting by dynamic secondary ion mass spectrometry (D-SIMS) the common secondary ions along with the corresponding rare secondary ions; and
(d) based upon the results obtained in step (c) determining the molecular atlas of said at least one sample.

5. A method for predicting a predisposition to a disease or for diagnosing a disease in a subject in need thereof comprising:
(a) contacting at least one sample from said subject with an array which comprises a substantially planar substrate having a conducting surface and a number of discrete areas containing probes being labeled with at least one rare, stable or unstable isotope or exogenous isotope;
(b) washing and drying the array;
(c) detecting and counting by dynamic secondary ion mass spectrometry (D-SIMS) the common secondary ions along with the corresponding rare secondary ions; and
(d) based upon the results obtained from step (c) predicting a predisposition to a disease, or for diagnosing a disease in said at least one sample from said subject in need thereof.

6. A method for monitoring the efficacy of a therapeutic agent administered to a subject to treat a disease comprising:
(a) contacting at least one sample from said subject with an array which comprises a substantially planar substrate having a conducting surface and a number of discrete areas containing probes being labeled with at least one rare, stable or unstable isotope or exogenous isotope;
(b) washing and drying the array;
(c) detecting and counting by dynamic secondary ion mass spectrometry (D-SIMS) the common secondary ions along with the corresponding rare secondary ions; and
(d) based upon the results obtained from step (c) monitoring the efficacy of a therapeutic agent administered to a subject to treat said disease.

7. A method for screening therapeutic agents comprising:
(a) contacting at least one sample with an array which comprises a substantially planar substrate having a conducting surface and a number of discrete areas containing probes being labeled with at least one rare, stable or unstable isotope or exogenous isotope;
(b) washing and drying the array;
(c) detecting and counting by secondary ion mass spectrometry (SIMS) the common secondary ions along with the corresponding rare secondary ions; and
(d) based upon the results obtained from step (c) screening for therapeutic agents in said at least one sample.

* * * * *